(12) United States Patent
Blacker et al.

(10) Patent No.: US 12,318,161 B2
(45) Date of Patent: Jun. 3, 2025

(54) ROBOTIC ACTUATION OF ELONGATED MEDICAL DEVICES

(71) Applicant: Corindus, Inc., Newton, MA (US)

(72) Inventors: Steven J. Blacker, Framingham, MA (US); Per Bergman, West Roxbury, MA (US)

(73) Assignee: Siemens Healthineers Endovascular Robotics, Inc., Newton, MA (US)

( * ) Notice: Subject to any disclaimer, the term of this patent is extended or adjusted under 35 U.S.C. 154(b) by 0 days.

(21) Appl. No.: 18/548,599

(22) PCT Filed: Oct. 5, 2022

(86) PCT No.: PCT/US2022/077563
§ 371 (c)(1),
(2) Date: Sep. 1, 2023

(87) PCT Pub. No.: WO2023/060099
PCT Pub. Date: Apr. 13, 2023

(65) Prior Publication Data
US 2024/0024055 A1    Jan. 25, 2024

Related U.S. Application Data

(60) Provisional application No. 63/262,108, filed on Oct. 5, 2021.

(51) Int. Cl.
*A61B 34/30* (2016.01)
*A61B 34/00* (2016.01)
*A61B 34/37* (2016.01)

(52) U.S. Cl.
CPC .............. *A61B 34/37* (2016.02); *A61B 34/25* (2016.02); *A61B 2034/301* (2016.02)

(58) Field of Classification Search
None
See application file for complete search history.

(56) References Cited

U.S. PATENT DOCUMENTS

| 5,944,689 A | 8/1999 | Houser et al. |
| 7,008,401 B2 | 3/2006 | Thompson et al. |

(Continued)

FOREIGN PATENT DOCUMENTS

| EP | 3457959 | 2/2020 |
| EP | 3533410 | 4/2022 |

(Continued)

OTHER PUBLICATIONS

International Search Report for Corresponding PCT Application No. PCT/US2022/077563, dated Dec. 15, 2022.

*Primary Examiner* — Aurelie H Tu

(57) ABSTRACT

A system comprises an EMD and coupled to a robotic drive. The EMD includes an external member defining a lumen and an internal member disposed in the lumen and coupled to a distal portion of the external member, and a linearly and rotationally-actuatable element coupled to the external member. The robotic drive includes a plurality of device modules, each of the plurality of device modules being independently linearly movable by the robotic drive, a first cassette coupled to a first one of the plurality of device modules and to the linearly and rotationally-actuatable element of the external member, and a second cassette coupled to a second one of the plurality of device modules and to the internal member.

18 Claims, 8 Drawing Sheets

(56) References Cited

U.S. PATENT DOCUMENTS

| | | |
|---|---|---|
| 7,011,655 B2 | 3/2006 | Thompson et al. |
| 7,276,044 B2 | 10/2007 | Ferry et al. |
| 7,351,214 B2 | 4/2008 | Burgermeister |
| 7,371,248 B2 | 5/2008 | Dapolito et al. |
| 7,766,856 B2 | 8/2010 | Ferry et al. |
| 7,803,130 B2 | 9/2010 | Ryan et al. |
| 7,974,681 B2 | 7/2011 | Wallace et al. |
| 7,998,020 B2 | 8/2011 | Kidd et al. |
| 8,021,326 B2 | 9/2011 | Moll et al. |
| 8,108,069 B2 | 1/2012 | Stahler et al. |
| 8,114,097 B2 | 2/2012 | Brock et al. |
| 8,211,084 B2 | 7/2012 | Kassab et al. |
| 8,257,302 B2 | 9/2012 | Beyar et al. |
| 8,317,744 B2 | 11/2012 | Kirschenman |
| 8,390,438 B2 | 3/2013 | Olson et al. |
| 8,460,236 B2 | 6/2013 | Roelle et al. |
| 8,551,084 B2 | 10/2013 | Hauck et al. |
| 8,603,068 B2 | 12/2013 | Weitzner et al. |
| 8,615,288 B2 | 12/2013 | Govari et al. |
| 8,684,953 B2 | 4/2014 | Cabiri |
| 8,740,840 B2 | 6/2014 | Foley et al. |
| 8,790,297 B2 | 7/2014 | Bromander et al. |
| 9,005,217 B2 | 4/2015 | Govari et al. |
| 9,066,740 B2 | 6/2015 | Carlson et al. |
| 9,138,566 B2 | 9/2015 | Cabiri |
| 9,220,568 B2 | 12/2015 | Bromander et al. |
| 9,295,527 B2 | 3/2016 | Kirschenman et al. |
| 9,320,573 B2 | 4/2016 | Sandhu et al. |
| 9,333,324 B2 | 5/2016 | Cohen et al. |
| 9,545,246 B2 | 1/2017 | Lavender |
| 9,586,029 B2 | 3/2017 | Shekalim et al. |
| 9,763,650 B2 | 9/2017 | Chen et al. |
| 9,814,490 B2 | 11/2017 | Neoh et al. |
| 10,010,700 B2 | 7/2018 | Romoscanu |
| 10,130,242 B2 | 11/2018 | Ostrovsky et al. |
| 10,149,728 B2 | 12/2018 | Bencteux et al. |
| 10,352,411 B2 | 7/2019 | Fojtik |
| 10,357,230 B2 | 7/2019 | Bolduc |
| 10,448,811 B2 | 10/2019 | London Brown et al. |
| 10,451,409 B2 | 10/2019 | Tojo et al. |
| 10,456,556 B2 | 10/2019 | Cabiri |
| 10,463,835 B2 | 11/2019 | Jungles |
| 10,470,793 B2 | 11/2019 | McArthur et al. |
| 10,478,595 B2 | 11/2019 | Kokish |
| 10,500,373 B2 | 12/2019 | Barrish et al. |
| 10,507,037 B2 | 12/2019 | Doud et al. |
| 10,542,878 B2 | 1/2020 | Dewaele et al. |
| 10,549,071 B2 | 2/2020 | Falb et al. |
| 10,632,287 B2 | 4/2020 | Romoscanu et al. |
| 10,667,673 B2 | 6/2020 | Su et al. |
| 10,695,533 B2 | 6/2020 | DeBoeuf et al. |
| 10,695,536 B2 | 6/2020 | Weitzner et al. |
| 10,709,510 B2 | 7/2020 | Kottenstette |
| 10,744,301 B2 | 8/2020 | Pachecho et al. |
| 10,799,305 B2 | 10/2020 | Murphy et al. |
| 10,799,677 B2 | 10/2020 | Khuu et al. |
| 10,806,897 B2 | 10/2020 | Furnish |
| 10,813,708 B2 | 10/2020 | Reinstein et al. |
| 10,828,468 B2 | 11/2020 | Selkee |
| 10,835,716 B2 | 11/2020 | Kim et al. |
| 10,933,221 B2 | 3/2021 | Lepak et al. |
| 10,959,789 B2 | 3/2021 | Yi et al. |
| 10,994,097 B2 | 5/2021 | Ludwin et al. |
| 11,076,924 B2 | 8/2021 | Kim et al. |
| 11,141,566 B2 | 10/2021 | Cabiri |
| 11,147,950 B2 | 10/2021 | Destrebecq et al. |
| 11,185,666 B2 | 11/2021 | Choi et al. |
| 11,187,307 B2 | 11/2021 | Asselin et al. |
| 11,213,356 B2 | 1/2022 | Tanner et al. |
| 11,229,775 B2 | 1/2022 | Kim et al. |
| 11,234,767 B2 | 2/2022 | Viswanathan et al. |
| 11,266,424 B2 | 3/2022 | Hofmann et al. |
| 11,272,995 B2 | 3/2022 | Landey et al. |
| 11,273,038 B2 | 3/2022 | Tang et al. |
| 11,278,703 B2 | 3/2022 | Kokish et al. |
| 11,291,515 B2 | 4/2022 | Sharon et al. |
| 11,298,198 B2 | 4/2022 | Fournier et al. |
| 11,298,505 B2 | 4/2022 | Bailey et al. |
| 11,311,699 B2 | 4/2022 | Weisz et al. |
| 11,318,302 B2 | 5/2022 | Asleson et al. |
| 11,337,764 B2 | 5/2022 | Robocath |
| 2004/0059260 A1 | 3/2004 | Truwit |
| 2004/0254566 A1 | 12/2004 | Plicchi et al. |
| 2005/0020998 A1 | 7/2005 | Bonnette et al. |
| 2005/0171508 A1 | 8/2005 | Gilboa et al. |
| 2005/0245862 A1 | 11/2005 | Seward et al. |
| 2006/0146010 A1 | 7/2006 | Schneider |
| 2007/0239140 A1 | 10/2007 | Chechelski et al. |
| 2009/0012533 A1 | 1/2009 | Barbagli et al. |
| 2009/0082722 A1 | 3/2009 | Munger et al. |
| 2010/0204646 A1 | 8/2010 | Plicchi et al. |
| 2011/0028894 A1* | 2/2011 | Foley ............... A61M 25/0136 |
| | | 604/95.01 |
| 2011/0077591 A1 | 3/2011 | Plicchi et al. |
| 2011/0144576 A1 | 6/2011 | Rothe et al. |
| 2011/0144658 A1 | 6/2011 | Wenderow et al. |
| 2011/0238010 A1 | 9/2011 | Kirschenman et al. |
| 2012/0158011 A1 | 6/2012 | Sandhu et al. |
| 2012/0226227 A1* | 9/2012 | Weitzner ......... A61B 17/12136 |
| | | 604/95.01 |
| 2012/0245595 A1 | 9/2012 | Kesavadas et al. |
| 2012/0330335 A1 | 12/2012 | Shekalim et al. |
| 2013/0012380 A1 | 5/2013 | Comber et al. |
| 2013/0172713 A1* | 7/2013 | Kirschenman ......... A61B 5/283 |
| | | 600/585 |
| 2013/0304034 A1 | 11/2013 | Cabiri |
| 2013/0304035 A1 | 11/2013 | Cabiri |
| 2014/0276392 A1 | 9/2014 | Wong et al. |
| 2014/0276647 A1 | 9/2014 | Yu |
| 2014/0277333 A1* | 9/2014 | Lewis .................. A61B 34/30 |
| | | 623/1.11 |
| 2014/0343457 A1 | 11/2014 | Shekalim et al. |
| 2014/0350568 A1 | 11/2014 | Shekalim et al. |
| 2015/0073340 A1 | 3/2015 | Pacheco et al. |
| 2015/0073342 A1 | 3/2015 | Pacheco et al. |
| 2015/0080907 A1* | 3/2015 | Herrell ................ A61B 1/0016 |
| | | 606/130 |
| 2015/0009465 A1 | 4/2015 | Pacheco et al. |
| 2015/0090057 A1 | 4/2015 | Pacheco et al. |
| 2015/0099997 A1 | 4/2015 | Cabiri |
| 2015/0223832 A1* | 8/2015 | Swaney ............... A61B 34/10 |
| | | 703/1 |
| 2015/0313677 A1 | 11/2015 | Kidd et al. |
| 2015/0314107 A1 | 11/2015 | Rothe et al. |
| 2016/0038002 A1 | 2/2016 | Peters et al. |
| 2016/0271368 A1* | 9/2016 | Falb ................ A61M 25/09041 |
| 2016/0310702 A1 | 10/2016 | Cabiri |
| 2017/0252025 A1 | 9/2017 | Cabiri et al. |
| 2017/0348060 A1 | 12/2017 | Blacker |
| 2017/0360372 A1 | 12/2017 | Hauck et al. |
| 2017/0367776 A1 | 12/2017 | Kwok et al. |
| 2018/0064910 A1 | 3/2018 | Tegg |
| 2018/0125596 A1 | 5/2018 | He et al. |
| 2018/0126122 A1 | 5/2018 | Cabiri |
| 2018/0185104 A1 | 7/2018 | Olson et al. |
| 2018/0214675 A1 | 8/2018 | Shekalim et al. |
| 2019/0000568 A1 | 1/2019 | Connolly et al. |
| 2019/0076092 A1 | 3/2019 | Saroha et al. |
| 2019/0105112 A1 | 4/2019 | Popovic et al. |
| 2019/0111237 A1 | 4/2019 | Cabiri |
| 2019/0254690 A1 | 8/2019 | Cabiri et al. |
| 2019/0255289 A1 | 8/2019 | Cabiri |
| 2019/0307987 A1 | 10/2019 | Yu |
| 2019/0343404 A1 | 11/2019 | Shekalim et al. |
| 2019/0388164 A1 | 12/2019 | Gruionu et al. |
| 2020/0000539 A1 | 1/2020 | Sholev et al. |
| 2020/0060820 A1 | 2/2020 | Ben-Zvi et al. |
| 2020/0129252 A1 | 4/2020 | Kokish et al. |
| 2020/0129740 A1 | 4/2020 | Kottenstette et al. |
| 2020/0178990 A1 | 6/2020 | Chu |
| 2020/0179649 A1 | 6/2020 | Kern et al. |
| 2020/0188635 A1 | 6/2020 | Barrish et al. |
| 2020/0197111 A1 | 6/2020 | Kim et al. |
| 2020/0237440 A1 | 7/2020 | Zabar et al. |

(56) References Cited

U.S. PATENT DOCUMENTS

| | | | |
|---|---|---|---|
| 2020/0246089 A1 | 8/2020 | Schlenk et al. |
| 2020/0282181 A1 | 9/2020 | Cabiri |
| 2020/0297442 A1 | 9/2020 | Adebar et al. |
| 2020/0297971 A1 | 9/2020 | Beeckler et al. |
| 2020/0337585 A1 | 10/2020 | Shochat et al. |
| 2020/0360659 A1 | 11/2020 | Wong et al. |
| 2020/0405182 A1 | 12/2020 | Hoitink et al. |
| 2020/0405413 A1 | 12/2020 | Kokish et al. |
| 2021/0023337 A1 | 1/2021 | DeBuys et al. |
| 2021/0045764 A1 | 2/2021 | Sholev et al. |
| 2021/0060310 A1 | 3/2021 | Kim et al. |
| 2021/0077209 A1 | 3/2021 | Yu |
| 2021/0236105 A1 | 8/2021 | Hansen et al. |
| 2021/0236775 A1 | 8/2021 | Schultz |
| 2021/0236778 A1 | 8/2021 | Kim et al. |
| 2022/0111176 A1 | 4/2022 | Dale et al. |
| 2022/0117683 A1 | 4/2022 | Schnur et al. |
| 2022/0211452 A1 | 7/2022 | Corindus |

FOREIGN PATENT DOCUMENTS

| | | |
|---|---|---|
| JP | 2017516604 | 6/2017 |
| WO | 9424946 | 11/1994 |
| WO | 2020105228 | 5/2020 |
| WO | 2021011518 | 1/2021 |
| WO | 2021011533 | 1/2021 |
| WO | 2021011551 | 1/2021 |
| WO | 2021011554 | 1/2021 |
| WO | 2021065312 | 4/2021 |
| WO | 2021117724 | 6/2021 |

* cited by examiner

ROBOTIC ACTUATION OF ELONGATED MEDICAL DEVICES

CROSS-REFERENCE TO RELATED APPLICATIONS

This application claims priority to U.S. Provisional Application No. 63/262,108, filed Oct. 5, 2021, the contents of which are incorporated herein by reference for all purposes.

FIELD

Embodiments relate generally to the field of robotic medical procedure systems and, in particular, to systems, apparatus and methods for robotically controlling the movement of one or more elongated medical devices (EMDs) during robotic interventional medical procedures.

BACKGROUND

Catheters and other EMDs may be used during medical procedures for the diagnosis and/or treatment of diseases of various vascular systems, including neurovascular intervention (NVI), percutaneous coronary intervention (PCI) and peripheral vascular intervention (PVI). These procedures typically involve navigating a guidewire through patient vasculature and advancing a catheter, valve, stent, etc. via the guidewire to deliver therapy.

A physician may use an imaging system to obtain a contrast-enhanced image for use in diagnosis, identification of lesion location(s) and determination of a path through which the guidewire or catheter may advance to the location of a target (e.g., a lesion). Contrast-enhanced images are also obtained while the physician manipulates the proximal end of the guidewire or catheter to direct the distal tip thereof into vessels which lie on the path to the target location and avoid advancing into side branches of the vasculature, while monitoring for complications such as perforation and dissection.

Flexibility of the catheter or other medical device is desired to facilitate negotiation of the vasculature. It is also desirable for the distal tip to be more bendable than the rest of the device, while still allowing the device to apply torque to the tip. Some conventional "steerable" catheters include multiple cables (sometimes referred to as push/pull wires) integrated into the wall of the catheter. By applying tension to the cables at the proximal end of such a catheter, the distal tip of the catheter can be bent in various directions to assist in navigating the vasculature when the catheter is advanced.

Some EMDs include an external member and an internal member coupled to a distal portion of the external member. The distal end is bent or otherwise deformed by causing relative motion between the external member and internal member. These EMDs advantageously present a smaller cross-section than the cable-based steerable EMDs described above.

Control of the distal tip requires manipulation of handheld features to manually rotate the external member with respect to the internal member and/or manually retract and insert the internal member with respect to the external member. Improved systems for control of such EMDs are desired, which may provide improved precision and/or accuracy of the relative movement between the external member and the internal member and, as a result, improved control over the distal tip or other actuatable device coupled thereto. Such improvements may result in increased procedure speed and improved safety.

BRIEF DESCRIPTION OF THE DRAWINGS

Embodiments will become more fully understood from the following detailed description, taken in conjunction with the accompanying drawings, wherein the reference numerals refer to like parts in which.

DETAILED DESCRIPTION

Figure 1:
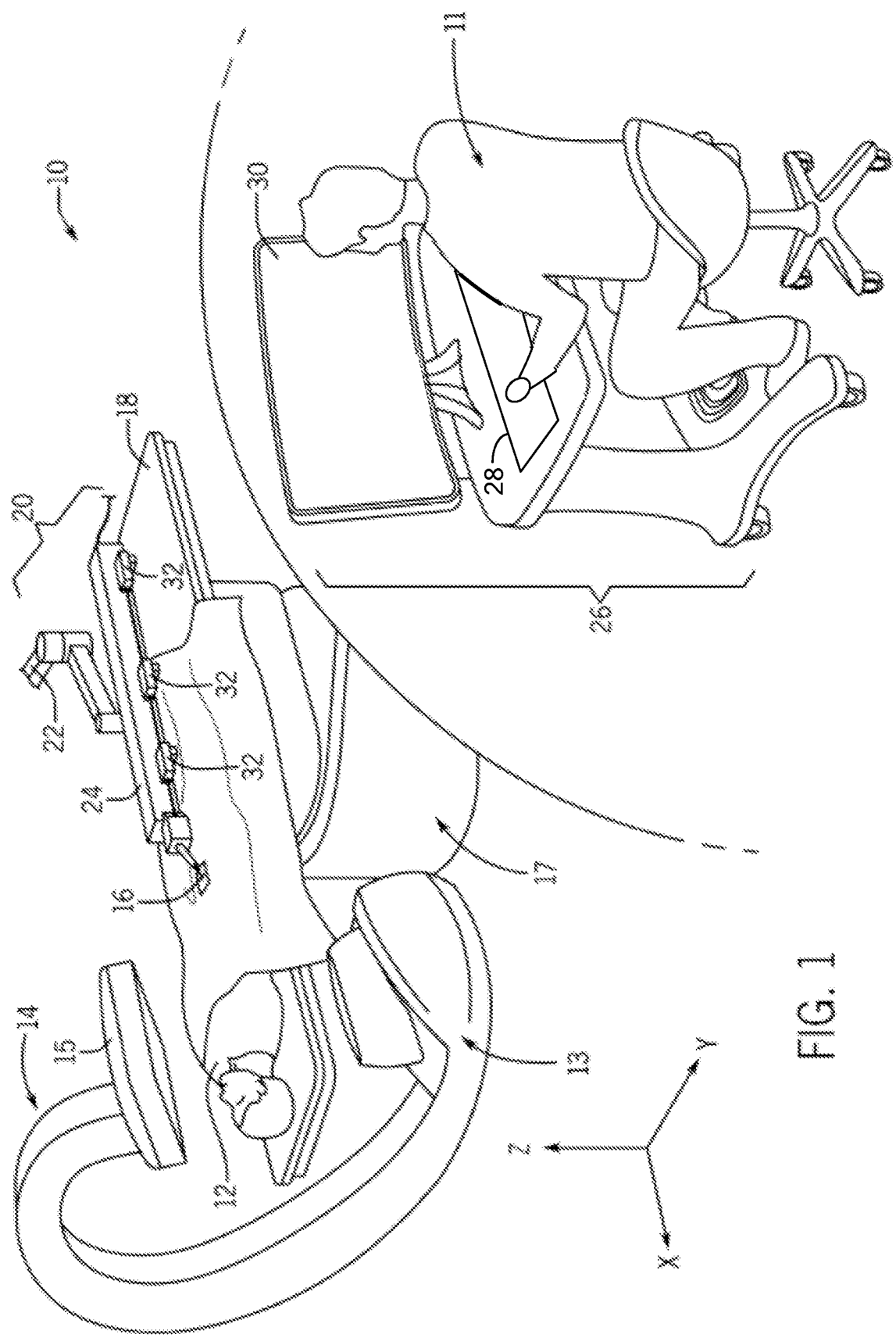
FIG. 1 is a perspective view of an exemplary catheter-based procedure system in accordance with some embodiments.

The following description is provided to enable any person in the art to make and use the described embodiments. Various modifications, however, will be readily-apparent to those in the art.

As used herein, EMD refers to, but is not limited to, catheters (e.g., guide catheters, microcatheters, balloon/stent catheters), wire-based devices (e.g., guidewires, microwires, proximal pushers for embolization coils, stent retrievers, self-expanding stents, flow divertors, etc.), and medical devices comprising any combination of these.

Some embodiments facilitate, in a robotic system, operation of an EMD including an inner member disposed within an external member lumen defined by an external member, and in which relative motion between the internal member and external member results in action at the distal portion of the EMD. The external member lumen need not extend the full length of the external member in some embodiments. The external member may comprise a tube but embodiments are not limited thereto. Either or both of the inner member and the external member may comprise multiple components.

Examples of the resulting action at the distal end include but are not limited to bending the distal portion in a case the EMD is a guidewire or catheter (e.g., Columbus by Rapid Medical, Bendit by Bendit), expanding or compressing the diameter of a distal portion as in an adjustable stent retriever (e.g., Tigertriever by Rapid Medical) controlling distal and proximal elements of a stent retriever (e.g., ThrombX retriever by ThrombX Medical) or an adjustable remodeling device (e.g., Comaneci by Rapid Medical, Cascade by Perflow Medical). The internal member and the external member may comprise separate respective EMDs. Such respective separate EMDs may be selectively operationally coupled at the distal portions thereof.

Some embodiments facilitate, in a robotic system, the application of such relative motion between an external member and an internal member disposed within the external member. The internal member may be partially disposed in the external member such that a portion of the internal member extends from one or both ends of the external member. The relative motion may be linear, rotational, or both. Relative rotational motion is achieved in some embodiments by rotating the proximal end of the external member and/or the proximal portion of the internal member in different directions and/or at different speeds. Relative linear motion is achieved by advancing or retracting the proximal portion of the external member and/or the internal member in different directions and/or at different speeds. Rotation of the whole EMD without causing relative rotational motion is achieved by rotating both proximal ends of the external member and internal member in the same direction (i.e., clockwise or counterclockwise) at the same angular rate. Advancement or retraction of the whole EMD without causing relative linear motion is achieved by moving both proximal ends of the external member and internal member in the same direction at the same speed.

According to some embodiments, relative rotational movement is facilitated by attaching a rotationally-actuatable element, such as but not limited to a gear, on the outer surface of one or both of the external member and the internal member. The rotationally-actuatable element may be attached to the outer surface at a location which results in engagement with a drive mechanism of a cassette into which the external member or internal member is loaded.

Relative linear movement may be facilitated by attaching a locating feature with bearing surfaces fore and aft to one or both of the external member and the internal member. The locating feature may be attached to a location which results in engagement with a feature of a cassette into which the external member or internal member is loaded such that the feature engages with the bearing surfaces to move the external member or internal member fore and aft as a result of linear movement of the cassette. In some embodiments, the bearing surfaces are integral or otherwise coupled to the rotationally-actuatable element.

According to some embodiments, the length of the internal member which protrudes from the external member when the internal member is not in tension to result in action at the distal portion of the EMD may be different from the length used for handheld operation. In particular, and according to some embodiments, length of the internal member may be determined so that the distance between its proximal end and the proximal end of the external member is at least as long as the minimum operational distance between respective mounting features of adjacent cassettes in which the external member and internal member are loaded.

Via manipulation of the external member and internal member of such an EMD simultaneously at the same or different rates, the action at the distal portion (e.g., bending, expansion, contraction) may occur faster than it would as a result of moving either the external member while the internal member is fixed or the internal member while the external member is fixed.

A robotic system can be calibrated to an input device to control the tip of the EMD accurately. For example, rotation of a knob on an input device by 60 degrees may cause a 60-degree bend or an input device is moved to correspond accurately to the desired radius of curvature of the EMD's distal tip. A specific radius of curvature may be utilized to match the vessel radius of curvature to maintain the device in a particular location (e.g., when deploying therapy which may move the other devices).

Tracking of the distal portion of the EMD by an imaging system (e.g., a fluoroscopy system) may allow automatic control to advance the EMD and bend the distal portion so as to navigate the EMD to a target without human intervention. If the three-dimensional centerline of the desired vessel pathway to a target is known, then the robotic system could programmatically bend the EMDs distal tip while the EMD is advanced to follow the vessel pathway to the target.

Robotic actuation of an EMD may generally allow coordination of multiple successive and/or simultaneous inserting, bending and/or rotating motions to navigate the EMD to select a vessel, advance through a tortuous or a narrowed vessel, or stay on a desired path (i.e., avoid moving into an undesired side branch). Robotic actuation according to some embodiments may cause the EMDs distal tip to undulate (with or without rotation, reciprocating rotation or reciprocating advancement) to reduce friction on the vessel walls so as to facilitate advancement or retraction of the EMD and/or of another adjacent or coaxial EMD through a tortuous or a narrowed vessel section.

According to some embodiments, robotically-actuated motions of the distal tip of an EMD as described herein can be coordinated with other EMDs. For example, an EMD may be disposed with the lumen of an aspiration catheter and controlled as described herein to assist advancement of the aspiration catheter to a clot without requiring the aspiration catheter to cross the clot and risk fragmentation of the clot.

Bending a distal tip of an EMD as described here may be used to avoid vessel damage as when a guidewire distal tip is bent into a J-configuration so that, when advanced, the tip is prevented from entering a side branch and perforating arteries which may not be angiographically visualized in an NVI. The J-configuration can also be used as knuckle to perform a sub-intimal dissection in order to move past a CTO (chronic total occlusion) in a coronary procedure.

The relative motion facilitated by some embodiments may be limited, mechanically and/or via software, to either prevent vessel injury or damage the EMD itself. In some embodiments, a sensor installed on the EMD or in the rotational and/or linear motion actuator to measure force and the measurement is used to limit the amount of force imposed on the vessel or the device. The sensor could measure strain as with a strain gauge or fiber Bragg grating integrated into the EMD or the actuator.

FIG. 1 is a perspective view of an exemplary catheter-based procedure system 10 in accordance with some embodiments. Catheter-based procedure system 10 may be used to perform catheter-based medical procedures, e.g., percutaneous intervention procedures such as a PCI (e.g., to treat STEMI), an NVI (e.g., to treat an emergent large vessel occlusion (ELVO)), PVIs (e.g., for critical limb ischemia (CLI), etc.). Catheter-based medical procedures may include diagnostic catheterization procedures during which one or more catheters or other EMDs are used to aid in the diagnosis of a patient's disease. For example, during one embodiment of a catheter-based diagnostic procedure, a contrast media is injected into one or more arteries through a catheter and an image of the patient's vasculature is acquired whole the contrast media resides therein.

Catheter-based medical procedures may also include catheter-based therapeutic procedures (e.g., angioplasty, stent placement, treatment of peripheral vascular disease, clot removal, arterial venous malformation therapy, treatment of aneurysm, etc.) during which a catheter (or other EMD) is used to treat a disease. Therapeutic procedures may be enhanced by the inclusion of adjunct devices 54 (shown in FIG. 2) such as, for example, intravascular ultrasound (IVUS), optical coherence tomography (OCT), fractional flow reserve (FFR), etc. It should be noted, however, that one in the art would recognize that certain specific percutaneous intervention devices or components (e.g., type of guidewire, type of catheter, etc.) may be selected based on the type of procedure that is to be performed. Catheter-based procedure system 10 can perform any number of catheter-based medical procedures with minor adjustments to accommodate the specific percutaneous intervention devices to be used in the procedures.

Catheter-based procedure system 10 includes, among other elements, a bedside unit 20 and a control station 26. Bedside unit 20 includes a robotic drive 24 and a positioning system 22 that are located adjacent to a patient 12. Patient 12 is supported on a patient table 18. The positioning system 22 is used to position and support the robotic drive 24. The positioning system 22 may be, for example, a robotic arm, an articulated arm, a holder, etc. The positioning system 22 may be attached at one end to, for example, a rail on the patient table 18, a base, or a cart. The other end of the positioning system 22 is attached to the robotic drive 24. The positioning system 22 may be moved out of the way (along with the robotic drive 24) to allow for the patient 12 to be placed on the patient table 18. Once the patient 12 is positioned on the patient table 18, the positioning system 22 may be used to situate or position the robotic drive 24 relative to the patient 12 for the procedure. In some embodiments, patient table 18 is operably supported by a pedestal 17, which is secured to the floor and/or earth. Patient table 18 is able to move with multiple degrees of freedom, for example, roll, pitch, and yaw, relative to the pedestal 17. Bedside unit 20 may also include controls and displays 46 (shown in FIG. 2). For example, controls and displays may be located on a housing of the robotic drive 24.

The term front will refer to the side of the robotic drive 24 that faces the patient 12 and away from the positioning system 22, while the term rear refers to the side of the robotic drive 24 that is closest to the positioning system 22. The terms top, up, and upper refer to the general direction away from the direction of gravity and the terms bottom, down, and lower refer to the general direction in the direction of gravity.

Generally, the robotic drive 24 may be equipped with the appropriate percutaneous interventional devices and accessories 48 (shown in FIG. 2) (e.g., EMDs including an internal member and an external member as described herein, guidewires, various types of catheters including balloon catheters, stent delivery systems, stent retrievers, embolization coils, liquid embolics, aspiration pumps, device to deliver contrast media, medicine, hemostasis valve adapters, syringes, stopcocks, inflation device, etc.) to allow the user or operator 11 to perform a catheter-based medical procedure via a robotic system by operating various controls of a control system as described herein such as the controls and input module located at the control station 26. Bedside unit 20, and in particular the robotic drive 24, may include any number and/or combination of components to provide bedside unit 20 with the functionality described herein. A user or operator 11 at control station 26 is referred to herein as the control station user, control station operator, user or operator. A user or operator at bedside unit 20 is referred to as bedside unit user or bedside unit operator.

Figure 3:
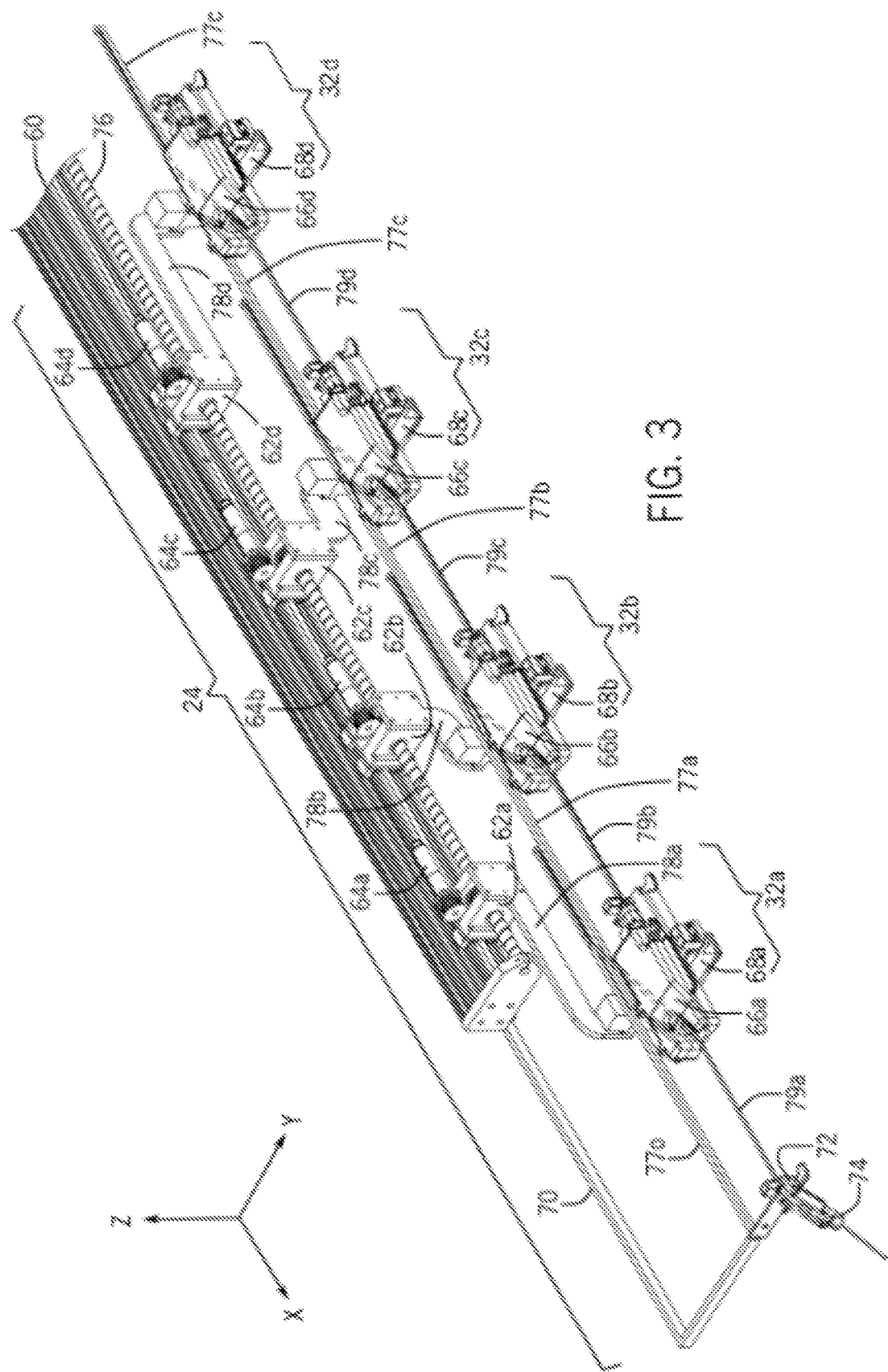
FIG. 3 is a perspective view of a robotic drive for a catheter-based procedure system in accordance with some embodiments.

The robotic drive 24 includes a plurality of device modules 32a-d mounted to a rail or linear member 60 (shown in FIG. 3). The rail or linear member 60 guides and supports the device modules. Each of the device modules 32a-d may be used to drive an EMD such as a catheter or guidewire. For example, the robotic drive 24 may be used to automatically feed a guidewire into a diagnostic catheter and into a guide catheter in an artery of the patient 12. One or more devices, such as an EMD, enter the body (e.g., a vessel) of the patient 12 at an insertion point 16 via, for example, an introducer sheath.

Bedside unit 20 is in communication with control station 26, allowing signals generated by the controls of control station 26 to be transmitted wirelessly or via hardwire to bedside unit 20 to control various functions of bedside unit 20, including functions of the robotic drive 24. As discussed below, control station 26 may include a control computing system 34 (shown in FIG. 2) or be coupled to the bedside unit 20 through a control computing system 34. Bedside unit 20 may also provide feedback signals (e.g., loads, speeds, operating conditions, warning signals, error codes, etc.) to control station 26, control computing system 34 (shown in FIG. 2), or both. Communication between the control computing system 34 and various components of the catheter-based procedure system 10 may be provided via a communication link that may be a wireless connection, cable connections, or any other means capable of allowing communication to occur between components.

The term local is used to refer to the location of the patient 12 and bedside unit 20. Catheter procedure system 10 may be operated by a control station 26 at the local site, a control station 26 at a remote site, or both a local control station 26 and a remote control station 26 at the same time. At a local site, user or operator 11 and control station 26 are located in the same room or an adjacent room to the patient 12 and bedside unit 20. As used herein, a local site is the location of the bedside unit 20 and a patient 12 or subject (e.g., animal or cadaver) and the remote site is the location of a user or operator 11 and a control station 26 used to control the bedside unit 20 remotely. The term remote is used to refer to locations that do not have physical access to the bedside unit 20 and/or patient 12 at a local site.

In some embodiments, the remote site and the local (patient) site are away from one another, for example, in different rooms in the same building, different buildings in the same city, different cities, or other different locations where the remote site does not have physical access to the bedside unit 20 and/or patient 12 at the local site.

Control station 26 includes input module 28 including controls configured according to some embodiments to receive user manipulations for controlling robotic drive 24 and/or various other components or systems of catheter-based procedure system 10. In the embodiment shown, control station 26 allows the user or operator 11 to control bedside unit 20 to perform a catheter-based medical procedure. For example, input module 28 may be configured to cause bedside unit 20 to perform various tasks using percutaneous intervention devices (e.g., EMDs) interfaced with the robotic drive 24 (e.g., to advance, retract, or rotate a guidewire, advance, retract or rotate a catheter, inflate or deflate a balloon located on a catheter, position and/or deploy a stent, position and/or deploy a stent retriever, position and/or deploy a coil, inject contrast media into a catheter, inject liquid embolics into a catheter, inject medicine or saline into a catheter, aspirate on a catheter, or to perform any other function that may be performed as part of a catheter-based medical procedure). Robotic drive 24 includes various drive mechanisms to cause movement (e.g., linear and rotational movement) of the components of the bedside unit 20 including the percutaneous intervention devices in response to user manipulation of the controls of input module 28.

An input module 28 may include device selection buttons as described below to allow the operator 11 to select which of the percutaneous intervention devices loaded into the robotic drive 24 are controlled via user manipulation of input controls. Automated move buttons may be used to enable algorithmic movements that the catheter-based procedure system 10 may perform on a percutaneous intervention device without direct command from the user or operator 11.

An input module 28 may also include a balloon or stent control that is configured to instruct inflation or deflation of a balloon and/or deployment of a stent. An input module 28 may include one or more buttons, scroll wheels, joysticks, touch screen, etc. that is dedicated to instruct control of a particular component or components. In addition, one or more touch screens may display one or more icons (not shown) presenting relative positions of input modules 28 or various components of catheter-based procedure system 10. Such one or more touch screens may present a user interface for specifying and/or presenting a configuration of the controls of input module 28 and one or more functions, including but not limited to linear and/or rotational locking functions.

Control station 26 may include a display 30. In some embodiments, the control station 26 may include two or more displays 30. Display 30 may be configured to display information or patient specific data to the user or operator 11 located at control station 26. For example, display 30 may be configured to display image data (e.g., X-ray images, MRI images, CT images, ultrasound images, etc.), hemodynamic data (e.g., blood pressure, heart rate, etc.), patient record information (e.g., medical history, age, weight, etc.), lesion or treatment assessment data (e.g., IVUS, OCT, FFR, etc.). In addition, display 30 may be configured to display procedure specific information (e.g., procedural checklist, recommendations, duration of procedure, catheter or guidewire position, volume of medicine or contrast agent delivered, etc.). Further, display 30 may be configured to display information to provide the functionalities associated with control computing system 34 (shown in FIG. 2). Display 30 may include touch screen capabilities to provide some of the user input capabilities of the system.

Catheter-based procedure system 10 also includes an imaging system 14. Imaging system 14 may be any medical imaging system that may be used in conjunction with a catheter based medical procedure (e.g., non-digital X-ray, digital X-ray, CT, MRI, ultrasound, etc.). In an exemplary embodiment, imaging system 14 is a digital X-ray imaging device that is in communication with control station 26. In one embodiment, imaging system 14 may include a C-arm (shown in FIG. 1) that allows imaging system 14 to partially or completely rotate around patient 12 in order to obtain images at different angular positions relative to patient 12 (e.g., sagittal views, caudal views, anterior-posterior views, etc.). In one embodiment, imaging system 14 is a fluoroscopy system including a C-arm having an X-ray source 13 and a detector 15, also known as an image intensifier.

Imaging system 14 may be configured to acquire X-ray images of the appropriate area of patient 12 during a procedure. For example, imaging system 14 may be configured to acquire one or more X-ray images of the head to diagnose a neurovascular condition. Imaging system 14 may also be configured to take one or more X-ray images (e.g., real time images) during a catheter-based medical procedure to assist the operator 11 of control station 26 to properly position a guidewire, guide catheter, microcatheter, stent retriever, coil, stent, balloon, etc. during the procedure. The image or images may be displayed on display 30. For example, images may be displayed on display 30 to allow the user or operator 11 to accurately move a guide catheter or guidewire into the proper position.

In order to clarify directions, a rectangular coordinate system is introduced with X, Y, and Z axes. The positive X axis is oriented in a longitudinal (axial) distal direction, that is, in the direction from the proximal end to the distal end, stated another way from the proximal to distal direction. The Y and Z axes are in a transverse plane to the X axis, with the positive Z axis oriented up, that is, in the direction opposite of gravity, and the Y axis is automatically determined by right-hand rule.

Figure 2:
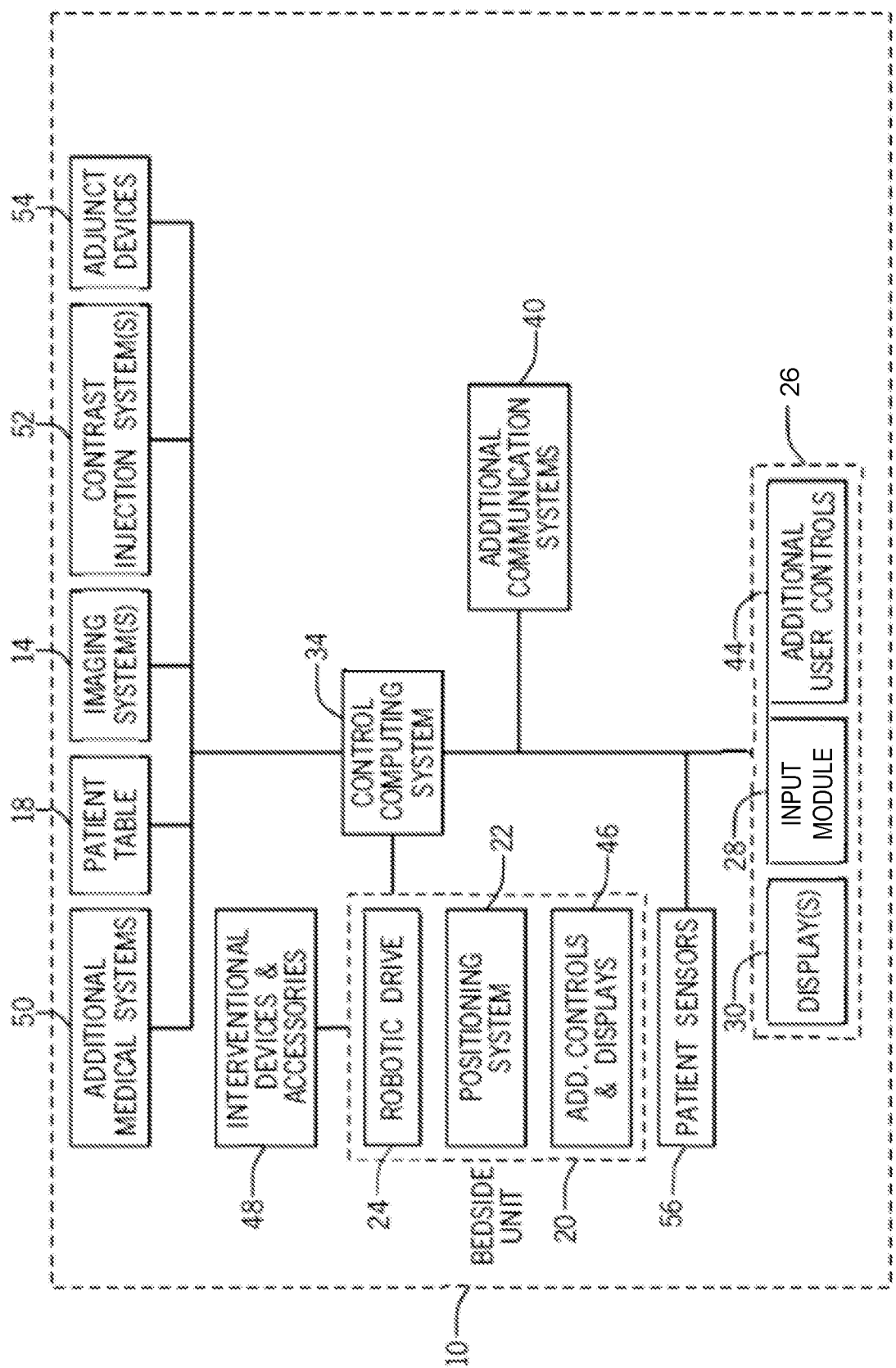
FIG. 2 is a schematic block diagram of an exemplary catheter-based procedure system in accordance with some embodiments.

FIG. 2 is a block diagram of catheter-based procedure system 10 in accordance with an exemplary embodiment. Catheter-procedure system 10 may include a control computing system 34. Control computing system 34 may physically be, for example, part of control station 26 (shown in FIG. 1). Control computing system 34 may generally comprise a computer processing unit suitable to provide catheter-based procedure system 10 with the various functionalities described herein. For example, control computing system 34 may be an embedded system, a dedicated circuit, a general-purpose system programmed with the functionality described herein, etc. Control computing system 34 is in communication with bedside unit 20, control station 38, additional communications systems 40 (e.g., a telepresence system, and patient sensors 56 (e.g., electrocardiogram (ECG) devices, electroencephalogram (EEG) devices, blood pressure monitors, temperature monitors, heart rate monitors, respiratory monitors, etc.).

Control computing system 34 is also in communication with imaging system 14, patient table 18, additional medical systems 50, contrast injection systems 52 and adjunct devices 54 (e.g., IVUS, OCT, FFR, etc.). The bedside unit 20 includes a robotic drive 24, a positioning system 22 and may include additional controls and displays 46. As mentioned above, the additional controls and displays may be located on a housing of the robotic drive 24. Interventional devices and accessories 48 (e.g., guidewires, catheters, etc.) interface to the bedside system 20. In some embodiments, interventional devices and accessories 48 may include specialized devices (e.g., EMDs including an internal member and an external member as described herein, IVUS catheter, OCT catheter, FFR wire, diagnostic catheter for contrast, etc.) which interface to their respective adjunct devices 54, namely, an IVUS system, an OCT system, and FFR system, etc.

In various embodiments, control computing system 34 is configured to receive and generate control signals based on user manipulation of the controls of input module 28 of control station 26, and/or based on information accessible to control computing system 34, such that a medical procedure may be performed using catheter-based procedure system 10.

Catheter-based procedure system 10 may be connected or configured to include any other systems and/or devices not explicitly shown. For example, catheter-based procedure system 10 may include image processing engines, data storage and archive systems, automatic balloon and/or stent inflation systems, medicine injection systems, medicine tracking and/or logging systems, user logs, encryption systems, systems to restrict access or use of catheter-based procedure system 10, etc.

FIG. 3 is a perspective view of a robotic drive 24 for a catheter-based procedure system 10 in accordance with some embodiments. Embodiments are not limited to the robotic drive 24 of FIG. 3. The robotic drive 24 of FIG. 3 includes multiple device modules 32a-d coupled to a linear member 60. Each device module 32a-d is coupled to the linear member 60 via a stage 62a-d moveably mounted to the linear member 60. A device module 32a-d may be connected to a stage 62a-d using a connector such as an offset bracket 78a-d. In another embodiment, the device module 32a-d is directly mounted to the stage 62a-d.

Each stage 62a-d may be independently actuated to move linearly along the linear member 60. Accordingly, each stage 62a-d (and the corresponding device module 32a-d coupled to the stage 62a-d) may independently move relative to each other and the linear member 60. A drive mechanism is used to actuate each stage 62a-d. In the embodiment shown in FIG. 3, the drive mechanism includes independent stage translation motors 64a-d coupled to each stage 62a-d and a stage drive mechanism 76, for example, a lead screw via a rotating nut, a rack via a pinion, a belt via a pinion or pulley, a chain via a sprocket, or the stage translation motors 64a-d may be linear motors themselves. In some embodiments, the stage drive mechanism 76 may be a combination of these mechanisms, for example, each stage 62a-d could employ a different type of stage drive mechanism. In some embodiments where the stage drive mechanism is a lead screw and rotating nut, the lead screw may be rotated and each stage 62a-d may engage and disengage from the lead screw to move, e.g., to advance or retract. In the embodiment shown in FIG. 3, the stages 62a-d and device modules 32a-d are in a serial drive configuration.

Each device module 32a-d includes a device module 68a-d and a cassette 66a-d mounted on and coupled to the device module 68a-d. In the embodiment shown in FIG. 3, each cassette 66a-d is mounted to the device module 68a-d in a vertical orientation. In other embodiments, each cassette 66a-d may be mounted to the device module 68a-d in other mounting orientations. Each cassette 66a-d is configured to interface with and support a proximal portion of an EMD (not shown). In addition, each cassette 66a-d may include elements to provide one or more degrees of freedom in addition to the linear motion provided by the actuation of the corresponding stage 62a-d to move linearly along the linear member 60. For example, the cassette 66a-d may include elements that may be used to rotate the EMD when the cassette is coupled to the device module 68a-d.

Each device module 68a-d includes at least one coupler to provide a drive interface to the mechanisms in each cassette 66a-d to provide the additional degree of freedom. Each cassette 66a-d also includes a channel in which a device support 79a-d is positioned, and each device support 79a-d is used to prevent an EMD from buckling. A support arm 77a, 77b, and 77c is attached to each device module 32a, 32b, and 32c, respectively, to provide a fixed point for support of a proximal end of the device supports 79b, 79c, and 79d, respectively. The robotic drive 24 may also include a device support connection 72 connected to a device support 79, a distal support arm 70 and a support arm $77_0$. Support arm $77_0$ is used to provide a fixed point for support of the proximal end of the distal-most support arm 79a housed in the distal most device module 32a. In addition, an introducer interface support (redirector) 74 may be connected to the device support connection 72 and an EMD (e.g., an introducer sheath). The configuration of robotic drive 24 has the benefit of reducing volume and weight of the drive robotic drive 24 by using actuators on a single linear member.

To prevent contaminating the patient with pathogens, healthcare staff use aseptic technique in a room housing the bedside unit 20 and the patient 12 or subject (shown in FIG. 1). A room housing the bedside unit 20 and patient 12 may be, for example, a cath lab or an angio suite. Aseptic technique consists of using sterile barriers, sterile equipment, proper patient preparation, environmental controls and contact guidelines. Accordingly, all EMDs and interventional accessories are sterilized and can only be in contact with either sterile barriers or sterile equipment. In some embodiments, a sterile drape (not shown) is placed over the non-sterile robotic drive 24. Each cassette 66a-d is sterilized and acts as a sterile interface between the draped robotic drive 24 and at least one EMD. Each cassette 66a-d can be designed to be sterile for single use or to be re-sterilized in whole or part so that the cassette 66a-d or its components can be used in multiple procedures.

As used herein, the term cassette generally refers to a component of a robotic drive system including components to support and move (e.g., rotate and/or translate) at least one EMD. A device module generally refers to a component of a robotic drive system that includes one or more motors with drive couplers which interface with the EMD-moving elements of the cassette. A cassette may provide a sterile interface between at least one EMD and a device module directly or through a device adapter. The term drive module refers to the combination of a device module and a cassette.

In some embodiments, an EMD is a catheter having a hub at a proximal end of the catheter and a flexible shaft extending from the hub toward the distal end of the catheter, wherein the shaft is more flexible than the hub. In one embodiment the catheter includes an intermediary portion that transitions between the hub and the shaft that has an intermediate flexibility that is less rigid than the hub and more rigid than the shaft. In some embodiments the intermediary portion is a strain relief.

The longitudinal axis of a member (for example, an EMD or other element in the catheter-based procedure system) is the line or axis along the length of the member that passes through the center of the transverse cross section of the member in the direction from a proximal portion of the member to a distal portion of the member. For example, the longitudinal axis of a guidewire is the central axis in the direction from a proximal portion of the guidewire toward a distal portion of the guidewire even though the guidewire may be non-linear in the relevant portion.

Linear movement of a member refers to translation of the member along the longitudinal axis of the member. For example, when the distal end of an EMD is linearly moved in a distal direction along its longitudinal axis into or further into the patient, the EMD is being advanced. When the distal end of an EMD is linearly moved in a proximal direction along its longitudinal axis out of or further out of the patient, the EMD is being withdrawn.

In this regard, linear insertion refers to inserting a first member into a second member along the longitudinal axis of the second member. For example, an EMD that is linear loaded in a collet is linear inserted in the collet. An example of linear insertion could be referred to as back loading a catheter on the proximal end of a guidewire. Lateral insertion refers to inserting a first member into a second member along a direction in a plane perpendicular to the longitudinal axis of the second member. Lateral insertion can also be referred to as radial loading or side loading.

Rotational movement of a member refers to the change in angular orientation of the member about the local longitudinal axis of the member. For example, rotational movement of an EMD corresponds to clockwise or counterclockwise rotation of the EMD about its longitudinal axis due to an applied torque. Continuous motion refers to motion that does not require a reset and is uninterrupted, while discrete motion refers to motion that requires a reset and is interrupted.

The terms distal and proximal define relative locations of two different features. With respect to a robotic drive, the terms distal and proximal are defined by the position of the robotic drive in its intended use relative to a patient.

When used to define a relative position, the distal feature is the feature of the robotic drive that is closer to the patient than a proximal feature when the robotic drive is in its intended in-use position. Within a patient, any vasculature landmark further away along the path from the access point is considered more distal than a landmark closer to the access point, where the access point is the point at which the EMD enters the patient. Similarly, the proximal feature is the feature that is farther from the patient than the distal feature when the robotic drive in its intended in-use position.

When used to define direction, the distal direction refers to a path on which something is moving or is aimed to move or along which something is pointing or facing from a proximal feature toward a distal feature and/or patient when the robotic drive is in its intended in-use position. The proximal direction is the opposite direction of the distal direction. For example, referring to FIG. 1, a robotic device is shown from the viewpoint of an operator facing a patient. In this arrangement, the distal direction is along the positive X coordinate axis and the proximal direction is along the negative X coordinate axis.

With respect to movement of modules, and referring to FIG. 3, an EMD is moved in a distal direction on a path toward a patient through the introducer interface support 74 which defines the distal end of the robotic drive 24. The proximal end of the robotic drive 24 is the point furthest from the distal end along the negative X axis.

With respect to positions of the individual modules, and also referring to FIG. 3, the most distal device module is the device module 32a closest to the distal end of the robotic drive 24. The most proximal device module is the device module 32d positioned furthest from the distal end of the robotic drive 24 along the negative X axis. The relative position of device modules is determined by their relative location to the distal end of the robotic drive. For example, device module 32b is distal to device module 32c.

With respect to distal/proximal portions, sections or ends of an EMD or the robotic drive, the portions of cassette 66a and device module 68a are defined by their relative location to the distal end of the robotic drive. For example, the distal end of cassette 66a is the portion of the cassette that is closest to the distal end of the robotic drive and the proximal end of cassette 66a is the portion of the cassette that is furthest from the distal end of the robotic drive along the negative X axis when the cassette is in-use position on device module 68a. Stated in another way, the distal end of cassette 66a is the portion of the cassette through which an EMD is closest to the path leading to a patient in the in-use position.

As previously discussed, embodiments of a control station 26 can include a variety of different input modules for controlling the bedside unit 20. Input modules can include a variety of different input controls (for example, buttons, scroll wheels, joysticks, etc.) that can be manipulated by a user to control (or, instruct) operation of the robotic drive 24. These input controls can be arranged in different layouts or patterns on the input module to facilitate desired functions and cooperative sequencing thereof to perform a desired task requiring independent (and sometimes simultaneous) movement of multiple EMDs and/or independent (and possibly simultaneous) movement of different portions of a same EMD as described herein.

Figure 4A:
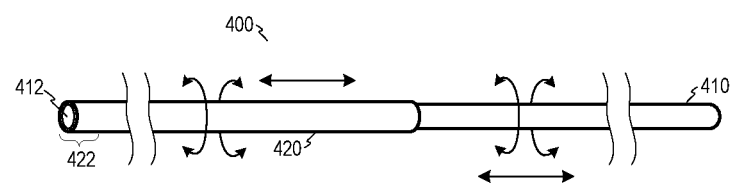
FIGS. 4A and 4B are perspective views of an EMD.
Figure 4B:
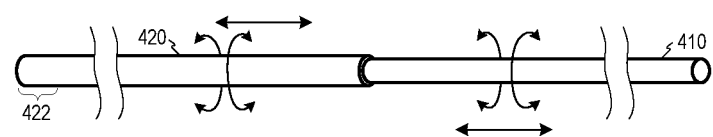

FIGS. 4A and 4B are perspective views of EMD 400 which may be used in conjunction with some embodiments. Embodiments are not limited to EMD 400. EMD 400 includes internal member 410 disposed inside external member 420. A distal portion 412 of internal member 410 is coupled to distal portion 422 of external member 420. The term "coupled" encompasses any attachment method, including but not limited to, welding, ultrasonic welding, thermal bonding, adhesive bonding, molding, and others. The coupling may occur at any surface disposed toward the distal ends of internal member 410 and external member 420. Although distal portion 412 of internal member is shown substantially flush with a distal end of external member 420, a distal portion of internal member 410 may extend past the distal end of external member 420 in some embodiments. A proximal portion of internal member 410 may extend past the proximal end of external member 420 in some embodiments. The portion of the internal member 410 may be operatively coupled to an actuatable element extending past the proximal end of external member 420.

Each of internal member 410 and external member 420 may be moved linearly in a proximal direction and a distal direction, and rotated clockwise and counterclockwise. The linear movement allows relative motion therebetween in a longitudinal direction. This relative motion and the coupling of the distal portions thereof causes bending of the distal ends as is known in the art. According to some embodiments, internal member 410 and external member 420 are also or alternatively configured for relative rotational movement. Such rotational movement may result in bending or other deformation of the distal ends thereof.

As is known in the art, at least one of internal member 410 and external member 420 may be slotted with slots to increase flexibility toward the distal ends thereof so as to improve steerability. The degree of flexibility may be determined by the number of slots, the spacing therebetween, the shape of the slots, the angle subtended by the slots, the thickness of and material, and other factors. Some embodiments achieve desired flexibility using a flexible material to serve in place of the above-described slotted portions and a rigid stiffener in place of the non-slotted portions.

In some embodiments, internal member 410 and external member 420 are composed of a suitably flexible, appropriate biocompatible material, including but not limited to, stainless steel (e.g., AISI 316), nitinol, cobalt-chromium alloy, nickel-titanium alloy, and others, plastics (e.g., nylon, polypropylene, and many others) or combinations thereof. The composition of internal member 410 may differ from the composition of external member 420. Either or both of internal member 410 and external member 420 may comprise machined features and/or component assemblies.

In some embodiments, internal member 410 defines a lumen throughout its length, which may define a lumen over the entire length of the EMD. During a procedure, fluid may be injected into the lumen from a proximal end of internal member 410. Fluid and material may also be extracted from vasculature (e.g., aspiration) via the lumen. A connector such as a luer connector may be coupled to a proximal end of internal member 410. Such a connector may facilitate a suitable fluid-tight connection between the lumen and an injection/suction/other system such as but not limited to a syringe, a hemostasis valve, a tube or other device.

Figure 5:
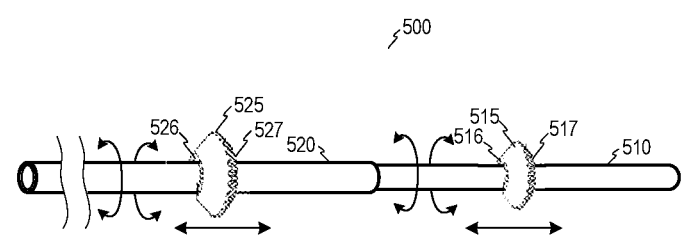
FIG. 5 is a perspective view of an EMD configured for robotic activation in accordance with some embodiments.

FIG. 5 is a perspective view of EMD 500 configured for robotic activation in accordance with some embodiments. As described with respect to EMD 400, EMD 500 includes internal member 510 disposed inside external member 520 and distal portions thereof are coupled to facilitate bending in response to relative movement. Internal member 510 and external member 520 of EMD 500 may exhibit any of the characteristics described above with respect to EMD 400 of FIGS. 4A and 4B.

Internal member 510 and external member 520 are movable relative to one another in a longitudinal direction. According to some embodiments, internal member 510 and external member 520 are also or alternatively configured for relative rotational movement. The relative movement and the coupling of the distal portions thereof causes bending and/or other deformation of the distal ends.

Actuatable elements 515 and 525 are coupled, respectively, to internal member 510 and to external member 520. Each of actuatable elements 515 and 525 may be independently driven in some embodiments to rotate the respective member/tube to which it is coupled. Such rotation may result in relative rotational movement between internal member 510 and external member 520.

Advantageously, rotation of internal member 510 and external member 520 in opposite directions can cause a particular magnitude of relative rotation faster than rotation of only one of internal member 510 and external member 520, assuming identical rotation speeds. Nevertheless, as will be described below, some embodiments may comprise rotation of one of internal member 510 and external member 520 while the other is fixed to prevent rotation thereof. Such embodiments may omit an element to actuate rotational movement from the internal member/external member which is held relatively fixed rotationally.

Although the rotationally-actuatable features of actuatable elements 515 and 525 are depicted as gear teeth, embodiments are not limited thereto. In one non-exhaustive embodiment, one or both of actuatable elements 515 and 525 comprise a pulley or an O-ring including surfaces to be frictionally engaged by a drive such as a belt, for example. In some embodiments, no rotational actuatable elements are coupled to internal member 510 and external member 520 but drive elements are used to impart rotation to internal member 510 and/or external member 520 via contact with a surface of internal member 510 and/or external member 520. Embodiments are not limited to one rotational actuatable element per member/tube.

Each of actuatable elements 515 and 525 comprise linearly-actuatable features 516, 517 and 526, 527 to facilitate linear movement of the respective internal member 510 and external member 520. For example, features of a cassette in which internal member 510 is mounted may engage against feature 516 when the cassette moves in a proximal direction, resulting in retraction of internal member 510 from external member 520, assuming the longitudinal position of external member 520 remains fixed. Conversely, features of the cassette in which internal member 510 is mounted may engage against feature 517 when the cassette moves in a distal direction, resulting in advancement of internal member 510 into external member 520, again assuming the longitudinal position of external member 520 remains fixed.

A feature of a cassette in which external member 520 is mounted may engage against feature 526 when the cassette moves in a proximal direction, resulting in movement of internal member 510 in the proximal direction, while a feature of the cassette may engage against feature 527 when the cassette moves in a distal direction, resulting in movement of external member 520 in a distal direction. Any of the above linear movements may be used to change a relative longitudinal relationship between internal member 510 and external member 520.

In some embodiments, a guidewire torquer (pin vise) or collet affixed to internal member 510 is used an a linearly- and/or rotationally-actuatable element to facilitate linear and/or rotational motion of internal member 510. In some embodiments, such a linearly- and/or rotationally-actuatable element is coupled to such a guidewire torquer (pin vise) or collet affixed to internal member 510.

Embodiments are not limited to a single actuatable element including features to provide rotational and linear motion. Embodiments are also not limited to rotational and linear motion of both internal member 510 and external member 520. For example, each of internal member 510 and external member 520 may be coupled to a respective zero or more actuatable elements which are robotically-drivable to cause rotation thereof, and to a respective zero or more actuatable elements which are robotically-drivable to cause linear movement thereof. As will be illustrated below, a rotationally- and/or linearly-actuatable element may be coupled to any suitable location of internal member 510 and/or external member 520.

Figure 6:
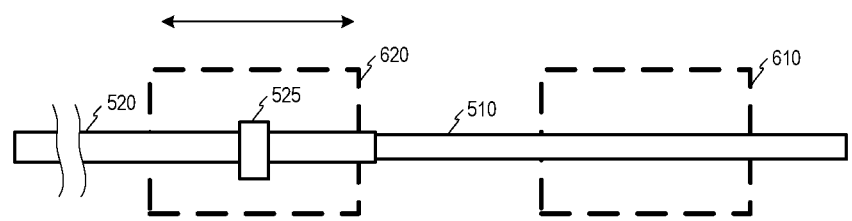
FIG. 6 is a schematic view of robotic actuation of an EMD in accordance with some embodiments.

FIG. 6 is a schematic view of robotic actuation of an EMD in accordance with some embodiments. External member 520 is loaded into cassette 620 of a robotic catheter system as described above with respect to cassettes 66a-66d of robotic drive 24. As described, mechanisms in cassette 620 are driven by a drive module. Driving of such mechanisms may drive actuatable element 525 to rotate external member 520 relative to internal member 510. In the FIG. 6 embodiment, cassette 620 may move linearly to move external member 520 linearly relative to internal member 510.

Figure 7:
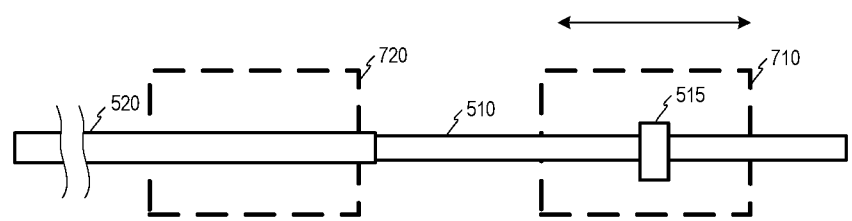
FIG. 7 is a schematic view of robotic actuation of an EMD in accordance with some embodiments.

FIG. 7 is a schematic view of robotic actuation of an EMD in accordance with some embodiments. Internal member 510 is loaded into cassette 710 of a robotic catheter system such that such mechanisms of cassette 710 may drive actuatable element 515 to rotate internal member 510 relative to external member 525. Cassette 710 may move linearly to move internal member 510 linearly relative to external member 520.

Figure 8:
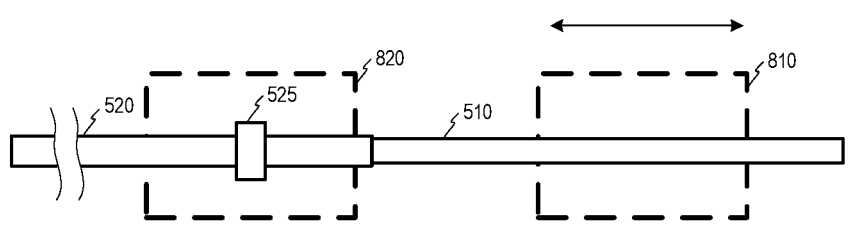
FIG. 8 is a schematic view of robotic actuation of an EMD in accordance with some embodiments.

FIG. 8 is a schematic view of robotic actuation of an EMD in accordance with some embodiments. External member 520 is loaded into cassette 820 of a robotic catheter system and mechanisms in cassette 820 may be driven to drive actuatable element 525 to rotate external member 520 relative to internal member 510. In the FIG. 8 embodiment, cassette 810 may move linearly to move internal member 510 linearly relative to external member 520.

Figure 9:
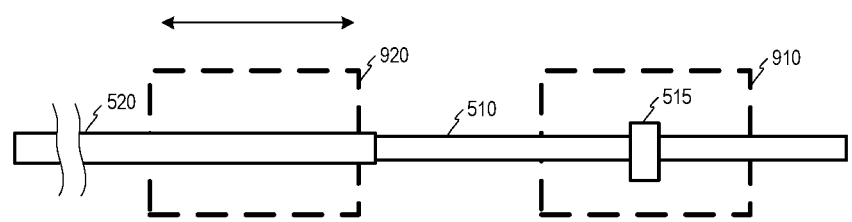
FIG. 9 is a schematic view of robotic actuation of an EMD in accordance with some embodiments.

As shown in FIG. 9, internal member 510 may be loaded into cassette 910 of a robotic catheter system such that such mechanisms of cassette 910 may drive actuatable element 515 to rotate internal member 510 relative to external member 520. Cassette 920 may move linearly to move external member 520 linearly relative to internal member 510.

Figure 10:
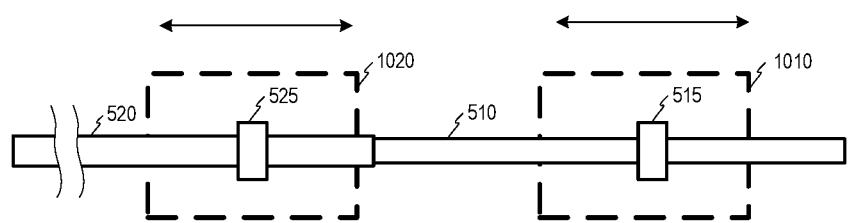
FIG. 10 is a schematic view of robotic actuation of an EMD in accordance with some embodiments.

FIG. 10 illustrates internal member 510 loaded into cassette 1010 and external member 520 loaded into cassette 1020. Each of cassettes 1010 and 1020 include mechanisms to drive respective actuatable elements 515 and 525 as described above with respect to FIG. 5. Each of cassettes 1010 and 1020 may move linearly in proximal and distal directions to move internal member 510 and external member 520 relative to one another. Such linear movement as described herein may be facilitated by features of a cassette which engage corresponding features of a linearly-actuatable element coupled to respective internal member 510 or external member 520 as described above with respect to FIG. 5. In some embodiments, the cassette features may comprise features which hold internal member 510 or external member 520 fixed with respect to the cassette while the cassette moves linearly.

As described above, relative linear and/or rotational motion of an internal member and an external member of an EMD may cause a desired action at the distal portion thereof. Some embodiments operate to receive a single operator command to perform the desired action (e.g., bend tip by a certain amount, expand clot retriever) and in response, control motors associated with each of the respective two cassettes which support the internal member and the external member to linearly and/or rotationally move the internal member and the external member to cause the required relative motion between the internal member and the external member which results in the desired action.

Figure 11:
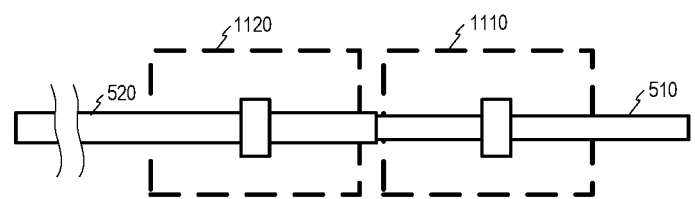
FIG. 11 is a schematic view of a fully inserted position of an EMD during robotic actuation thereof in accordance with some embodiments.

FIG. 11 illustrates cassettes 1110 and 1120 of a robotic drive positioned as close to one another as allowed by the robotic drive. Such a position determines a minimum length of a proximal portion of internal member 510 which extends from external member 520. The length should be sufficient for allowing loading of internal member within cassette 1110. Such a requirement may require increasing a length of internal member 510 with respect to conventionally-available steerable catheters including an internal member and an external member.

Figure 12:
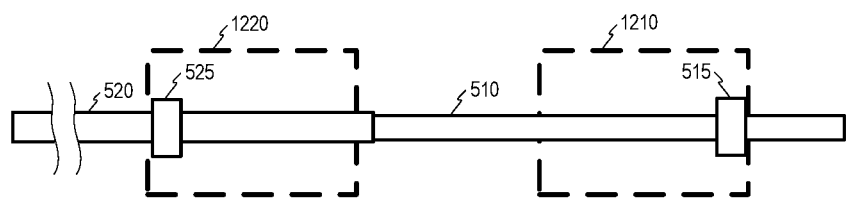
FIG. 12 is a schematic view of an EMD with actuatable elements mounted thereto in a first alternative arrangement in accordance with some embodiments.
Figure 13:
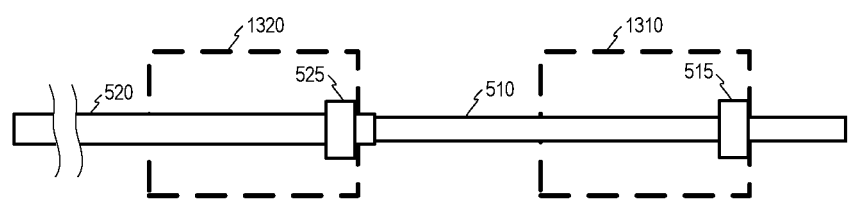
FIG. 13 is a schematic view of an EMD with actuatable elements mounted thereto in a second alternative arrangement in accordance with some embodiments.

FIGS. 12 and 13 illustrate different positions at which rotational actuatable elements 515 and 525 may be coupled to internal member 510 and external member 520 according to some embodiments. As mentioned above, zero or more actuatable elements may be coupled to any location of internal member 510 and/or external member 520. The actuatable elements are coupled to facilitate engagement with corresponding drive elements of cassettes 1210, 1220, 1310 and 1320.

Figure 14:
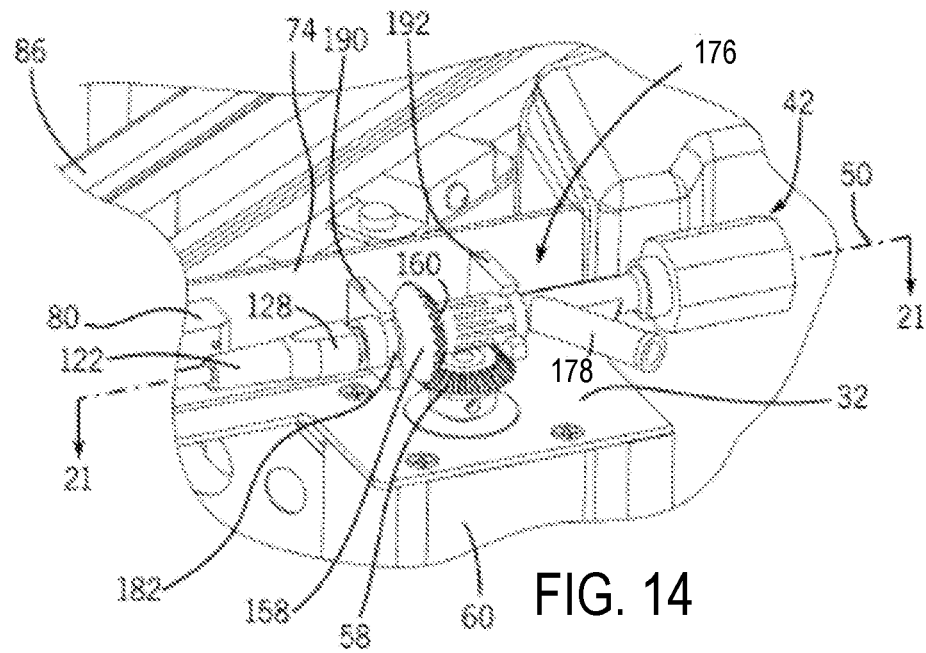
FIG. 14 is an isometric view of an actuatable element coupled to a drive member and rotatably coupling a hemostasis valve to a luer connector coupled to an internal member.
Figure 15:
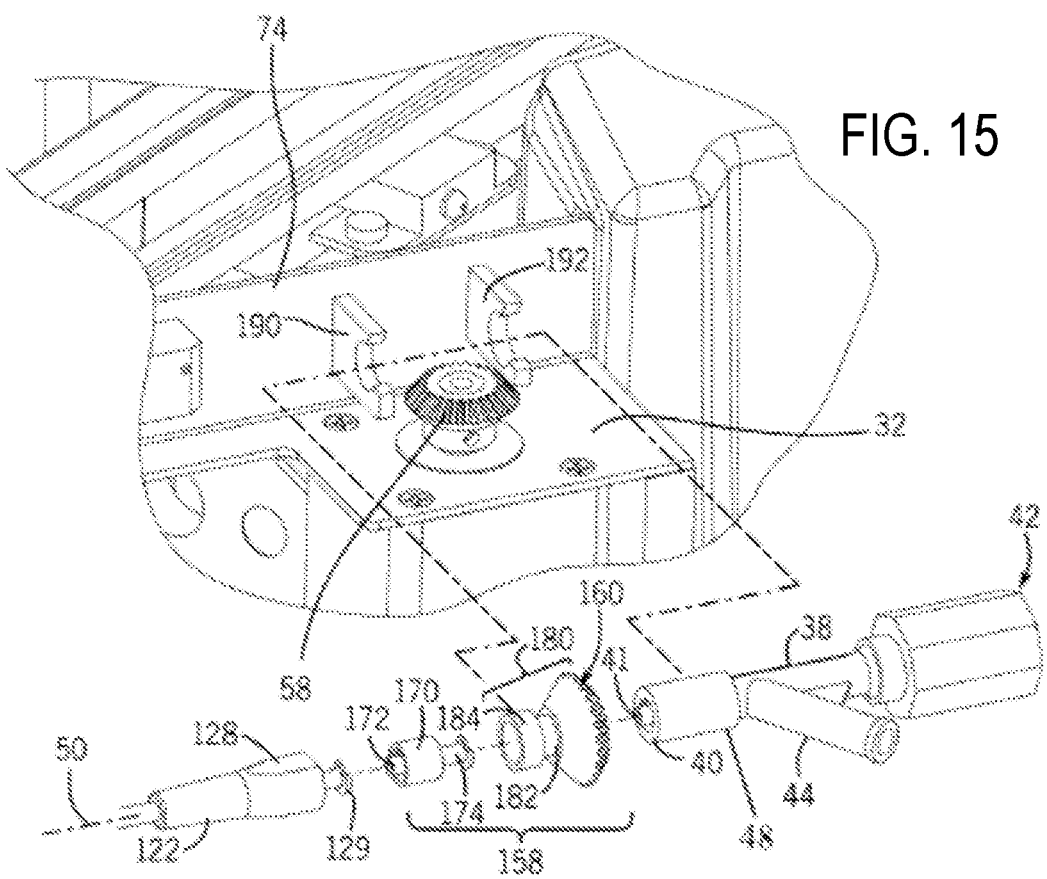
FIG. 15 is an exploded view of the internal member, luer connector, actuatable element and hemostasis valve of FIG. 14.

FIG. 14 is an isometric view and FIG. 15 is an exploded view of actuatable element assembly 158 coupled to internal member 122 including a lumen according to some embodiments. Gear teeth 160 of actuatable element assembly 158 engages drive member 58 of a cassette and rotatably couples assembly 158 to internal member 122. Such an arrangement forms a fluid tight rotational seal with male luer 41 of rotating element 40 and creates a continuous fluid path from hemostasis valve 176 to a lumen of internal member 122. In a case that internal member 122 does not include a lumen, hemostasis valve 176 and the luer connectors may be omitted.

Gear teeth 160 of actuatable element assembly 150 is driven by drive gear 58 to impart rotation to internal member 122 while isolating a body of hemostasis valve 176 from rotational motion such that the position of second leg 178 of valve 176 does not rotate when internal member 122 is rotated. Bracket 190 interacts with groove 182 to support assembly 158 as it rotates and is itself secured to either base 32 or wall 74. Hemostasis valve 176 is supported by bracket 192 that is itself secured to either base 32 or wall 74. Brackets 190 and 192 provide stability to longitudinal axis 50 of valve 176 and also serve as features to cause linear movement of internal member 122 when a cassette in which brackets 190 and 192 are disposed is moved linearly.

Computer-executable program code for controlling a catheter-based procedure system or presenting a user interface as described herein may be stored on non-transitory computer readable media. Computer readable media includes volatile and nonvolatile, removable, and non-removable media implemented in any method or technology for storage of information such as computer readable instructions, data structures, program modules or other data. Computer readable media includes, but is not limited to, random access memory (RAM), read-only memory (ROM), electrically erasable programmable ROM (EEPROM), flash memory or other memory technology, compact disk ROM (CD-ROM), digital versatile disks (DVD) or other optical storage, magnetic cassettes, magnetic tape, magnetic disk storage or other magnetic storage devices, or any other medium which can be used to store the desired instructions and which may be accessed by system 10 (shown in FIG. 1), including by internet or other computer network form of access.

What is claimed is:

1. A system comprising:
    an elongated medical device (EMD) comprising an external member defining a lumen and an internal member disposed in the lumen and coupled to a distal portion of the external member;
    a linearly-actuatable element coupled to the external member;
    a second linearly-actuatable element coupled to the internal member;
    a first cassette to support the external member and to move linearly in response to a first command; and
    a second cassette to support the internal member and to move linearly in response to a second command,
    wherein linear movement of the first cassette causes a feature of the first cassette to engage with the linearly-actuatable element to cause relative linear movement between the external member and the internal member, and
    wherein linear movement of the second cassette causes a feature of the second cassette to engage with the second linearly-actuatable element to cause second relative linear movement between the external member and the internal member.

2. The system according to claim 1, further comprising:
    a rotationally-actuatable element coupled to the external member; and
    the first cassette comprising a first drive element to drive the rotationally-actuatable element in response to a third command to cause relative rotational movement between the external member and the internal member.

3. The system according to claim 2, further comprising:
    a second rotationally-actuatable element coupled to the internal member; and the second cassette comprising a second drive element to drive the second rotationally-actuatable element in response to a fourth command to cause second relative rotational movement between the external member and the internal member.

4. The system according to claim 2, wherein the linearly-actuatable element and the rotationally-actuatable element comprise a same single element comprising linearly-actuatable features and rotationally-actuatable features.

5. The system according to claim 1, further comprising:
a rotationally-actuatable element coupled to the internal member; and
the second cassette comprising a drive element to drive the rotationally-actuatable element in response to the second command to cause relative rotational movement between the external member and the internal member.

6. The system according to claim 5, further comprising:
a second rotationally-actuatable element coupled to the external member,
the first cassette comprising a second drive element to drive the second rotationally-actuatable element in response to a fourth command to cause relative rotational movement between the external member and the internal member.

7. The system according to claim 6, wherein the linearly-actuatable element and the second rotationally-actuatable element comprise a same single element comprising linearly-actuatable features and rotationally-actuatable features.

8. A method comprising:
receiving a command to control a tip of an elongated medical device (EMD) comprising an external member defining a lumen and an internal member disposed in the lumen and coupled to a distal portion of the external member; and
in response to the command, causing relative linear movement between the external member and the internal member by:
controlling a robotic drive to move a first cassette supporting the external member linearly to cause a feature of the first cassette to engage with a linearly-actuatable element coupled to the external member; and
controlling a second robotic drive to move a second cassette supporting the internal member linearly to cause a feature of the second cassette to engage with a second linearly-actuatable element coupled to the internal member.

9. The method according to claim 8, further comprising:
in response to a second command, controlling the robotic drive to drive a rotationally-actuatable element coupled to the external member to cause relative rotational movement between the external member and the internal member.

10. The method according to claim 8, further comprising:
in response to a second command, controlling the robotic drive to drive a rotationally-actuatable element coupled to the internal member to cause relative rotational movement between the external member and the internal member.

11. The method according to claim 10, wherein the linearly-actuatable element and the rotationally-actuatable element comprise a same single element comprising linearly-actuatable features and rotationally-actuatable features.

12. The method according to claim 10, further comprising:
in response to the second command, controlling the robotic drive to drive a second rotationally-actuatable element coupled to the external member to cause relative rotational movement between the external member and the internal member.

13. The method according to claim 12, wherein the linearly-actuatable element and the rotationally-actuatable element comprise a same first single element comprising linearly-actuatable features and rotationally-actuatable features, and wherein the second linearly-actuatable element and the second rotationally-actuatable element comprise a same second single element comprising second linearly-actuatable features and second rotationally-actuatable features.

14. A system for controlling the tip of an elongated medical device (EMD), comprising:
an EMD comprising:
an external member defining a lumen and an internal member disposed in the lumen and coupled to a distal portion of the external member; and
a linearly- and rotationally-actuatable element coupled to the internal member; and
a robotic drive comprising:
a plurality of device modules, each of the plurality of device modules being independently linearly movable by the robotic drive;
a first cassette coupled to a first one of the plurality of device modules and to the linearly- and rotationally-actuatable element of the internal member; and
a second cassette coupled to a second one of the plurality of device modules and to the external member.

15. The system according to claim 14, wherein the linearly- and rotationally-actuatable element comprises linearly-actuatable features and rotationally-actuatable features.

16. The system according to claim 14, the EMD further comprising:
a second linearly actuatable element coupled to the external member,
wherein the second cassette is coupled to the second linearly actuatable element of the external member.

17. The system according to claim 16, wherein the linearly- and rotationally-actuatable element comprises linearly-actuatable features and rotationally-actuatable features, and
wherein the second linearly actuatable element comprises second linearly-actuatable features.

18. The system according to claim 16, wherein the first cassette is configured to drive the linearly and rotationally-actuatable element to rotate, and
wherein the second cassette is configured to drive the second linearly-actuatable element independently of rotation of the linearly and rotationally-actuatable element.

* * * * *